US010564156B2

(12) United States Patent
Merandon et al.

(10) Patent No.: US 10,564,156 B2
(45) Date of Patent: Feb. 18, 2020

(54) USE OF A COLORANT IN ORDER TO IMPROVE SIGNAL DETECTION IN AN ANALYSIS METHOD

(71) Applicant: BIO-RAD EUROPE GMBH, Basel (CH)

(72) Inventors: Bertrand Merandon, Chatillon (FR); Christophe Vedrine, Courbevoie (FR)

(73) Assignee: BIO-RAD EUROPE GMBH, Basel (CH)

( * ) Notice: Subject to any disclaimer, the term of this patent is extended or adjusted under 35 U.S.C. 154(b) by 107 days.

(21) Appl. No.: 15/302,526

(22) PCT Filed: Apr. 8, 2015

(86) PCT No.: PCT/EP2015/057633
§ 371 (c)(1),
(2) Date: Oct. 7, 2016

(87) PCT Pub. No.: WO2015/155248
PCT Pub. Date: Oct. 15, 2015

(65) Prior Publication Data
US 2017/0038377 A1   Feb. 9, 2017

(30) Foreign Application Priority Data

Apr. 9, 2014   (FR) ...................................... 14 53168

(51) Int. Cl.
*G01N 33/543*   (2006.01)
*G01N 21/64*   (2006.01)

(52) U.S. Cl.
CPC ... *G01N 33/54393* (2013.01); *G01N 21/6428* (2013.01); *G01N 33/54306* (2013.01); *G01N 2021/6441* (2013.01)

(58) Field of Classification Search
CPC ....... G01N 2021/6441; G01N 21/6428; G01N 33/543; G01N 33/54306; G01N 33/54393
(Continued)

(56) References Cited

U.S. PATENT DOCUMENTS 5,082,768 A   1/1992  Burd et al.
8,097,421 B2 * 1/2012  Koo ........................ B82Y 15/00
                                          356/335
(Continued)

FOREIGN PATENT DOCUMENTS

WO   WO 2015/150583   10/2015
WO   WO 2015/155254   10/2015
WO   WO 2015/155255   10/2015

OTHER PUBLICATIONS

Auld, D. S. et al. "Characterization of Chemical Libraries for Luciferase Inhibitory Activity" *J. Med. Chem*, 2008, pp. 2372-2386, vol. 51, No. 8.
(Continued)

*Primary Examiner* — Maureen Wallenhorst
(74) *Attorney, Agent, or Firm* — Saliwanchik, Lloyd & Eisenschenk

(57) ABSTRACT

The use of at least one colorant is provided in order to improve the detection of a signal corresponding to the presence of an analyte in a dot analysis method, in particular when the detection of the signal takes place in the presence of a liquid phase. Also provided is a dot analysis method that can be used to improve the detection of a signal corresponding to the presence of an analyte, in the presence of a liquid phase containing at least one colorant.

17 Claims, 5 Drawing Sheets

Figure 1:
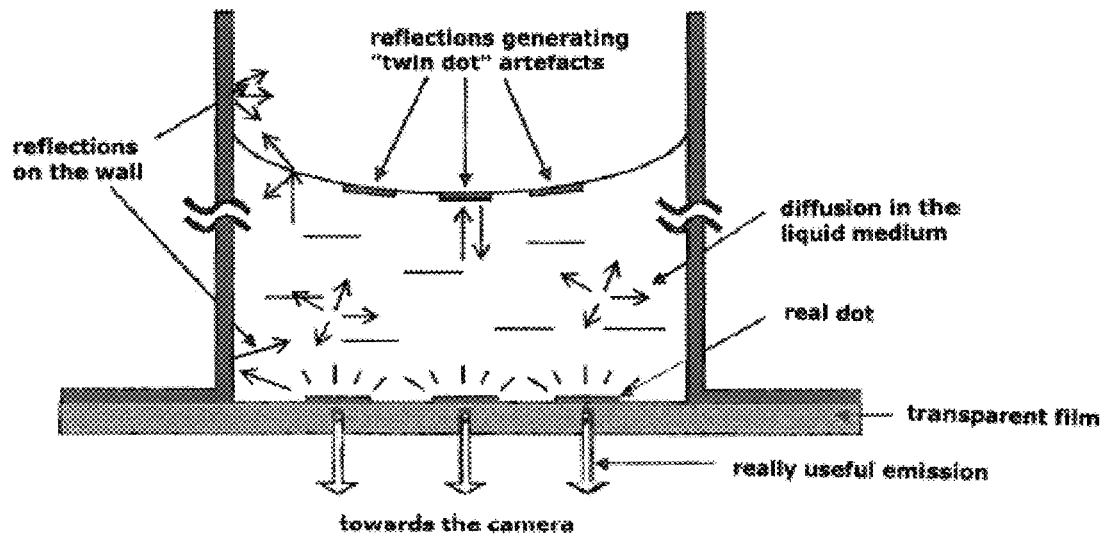

(58) Field of Classification Search
USPC ....... 436/518, 524, 63, 164, 172; 422/82.05,
422/82.08, 552, 553; 435/7.1, 7.5, 7.72,
435/7.9, 7.92, 7.94, 28, 287.1, 287.2,
435/288.3, 288.4, 288.7
See application file for complete search history.

(56) References Cited

U.S. PATENT DOCUMENTS

| | | | | |
|---|---|---|---|---|
| 8,163,562 | B2 * | 4/2012 | Knapp | C12Q 1/682 |
| | | | | 422/73 |
| 2001/0006820 | A1 | 7/2001 | Knapp et al. | |
| 2005/0026161 | A1 * | 2/2005 | Jablonski | C12Q 1/6804 |
| | | | | 435/6.12 |
| 2010/0267071 | A1 | 10/2010 | Akhavan-Tafti et al. | |
| 2011/0306511 | A1 * | 12/2011 | Lea | G01N 33/543 |
| | | | | 506/9 |
| 2015/0204862 | A1 * | 7/2015 | Fan | G01N 33/54366 |
| | | | | 506/9 |

OTHER PUBLICATIONS

Petersen, J. et al. "Comparison of Absorbance and Fluorescence Methods for Determining Liquid Dispensing Precision" *JALA*, Apr. 2005, pp. 82-87, vol. 10.
Written Opinion in International Application No. PCT/EP2015/057633, dated May 19, 2015, pp. 1-5.

* cited by examiner

USE OF A COLORANT IN ORDER TO IMPROVE SIGNAL DETECTION IN AN ANALYSIS METHOD

CROSS-REFERENCE TO RELATED APPLICATION

This application is the U.S. national stage application of International Patent Application No. PCT/EP2015/057633, filed Apr. 8, 2015.

TECHNICAL FIELD

The present invention relates to the improvement of the detection of a signal corresponding to the presence of an analyte in an analytical method, in particular when the analytical method requires signal acquisition in the presence of a liquid phase.

BACKGROUND ART

An analytical method allows to detect the possible presence of one or more analytes in a sample. An analytical method is generally performed on a solid support. Among the analytical methods, the multiplex analytical method allows to detect simultaneously the possible presence of several analytes within the same sample. A multiplex analytical method can be performed on a solid support comprising dots or else a plurality of beads.

Conventionally, an analytical method comprises a step of contacting a sample to be analyzed with at least one dot of a solid support or with beads comprising a specific capture ligand of an analyte to be detected, a step of adding a detection ligand specific for an analyte to be detected and coupled to a direct or indirect marker, any development step by addition of a reporter itself coupled to a direct or indirect marker, and a signal detection step (also called signal acquisition step). In the case of an indirect marker of the peroxidase enzyme type, adding a substrate of the enzyme allows an enzymatic reaction which leads to the production of a chemiluminescent compound. The signal is then detected by chemiluminescence.

Detecting a chemiluminescent signal requires, in principle, to perform signal acquisition in the presence of the substrate of the enzyme, i.e., in the presence of a liquid phase, in order to allow the continuous production of chemiluminescent compound.

Indeed, if a washing step is performed before the signal acquisition, the residual substrate is removed and the enzymatic reaction is stopped. However, it is known that the signal emitted by the chemiluminescent compound gradually fades away. Accordingly, the substrate of the enzyme must be present in a liquid phase in contact with the solid phase to allow a sufficiently stable and reproducible emission of the signal.

However, the acquisition of a signal at the dots of a well of a microplate in the presence of a liquid phase leads to light interference. Such light interference has several origins: first, photons emitted from dots close to the top of the well can interact with the compounds of the solution comprising the chemiluminescent compound and be disseminated in all directions; on the other hand, the photons may also be reflected by the walls of the well and the change of medium at the liquid/air interface, more precisely at the level of the meniscus formed by the interaction of the well wall and the solution comprising the chemiluminescent compound.

Such light interference can produce dots called "twin dots", slightly offset from the actual dots, a visible light ring on the periphery of the well, or even a light arc when the signal emitted at a dot is strong. Such light interference thus induces a problematic background noise, which can be the source of false negative or false positive results. For example, the light ring around the well can bias the background noise threshold, a weak signal then being drowned in the background noise. Light interference can also interfere with the verification of the absence of a failure in a dot effected by an annular measurement around a dot.

The document EP 0 165 072 discloses the use of an attenuator, preferably a mixture of red and yellow dyes, to suppress unwanted light and false positives results in a process involving a luminescent light emission. In this document, the unwanted light is adjacent to the measured surfaces. The test is performed in a hollow elongated pipette comprising a plurality of cotton yarns, each cotton yarn being linked to one type of antigen. The pipette is closed with a transparent window. The signal is revealed in the dark by pressing a film onto the surface of the pipette. The attenuator allows the suppression of false positives associated with non-specific binding of the HRP peroxidase enzyme to the cotton yarns.

Document U.S. Pat. No. 8,163,562 describes a test allowing to reduce undesirable light resulting from fluorescence of a solution in which is immersed a cellular compartment, which is preferably a cell. This undesired fluorescence originates especially from probes or chemical compounds used during the test. The signal to be detected is derived in turn from a photon producing agent located in the membrane compartment. For this purpose, a photon reducing agent impermeable to the membrane and not specifically binding to the membrane is used in the aqueous solution in contact with the outer surface of the membrane compartment. The photon reducing agent may be a dye or mixture of dyes.

There is therefore a need for solutions allowing to improve the detection of a signal corresponding to the presence of an analyte in the context of an analytical method performed on a dot or dots in which the acquisition of the signal at the dot or dots occurs in the presence of a liquid phase in order to secure the results obtained, avoiding false positive or false negative results.

DETAILED DESCRIPTION OF THE INVENTION

Surprisingly, in an analytical method performed on a dot or dots, the inventors have shown that the use of a dye, for example tartrazine, allows to remove, partially or entirely, unwanted light interference occurring usually during the acquisition of a signal in the presence of a liquid phase, without interfering, or interfering little, with the sensed signal corresponding to the presence of an analyte at a dot (e.g. luminescence and/or fluorescence), or with the possible detection of the fluorescence emitted by a fluorophore present as a control within the dot or dots. The use of a dye according to the invention thus enables the results obtained to be secured at the end of an analytical method, i.e., to ensure the reliability of said results obtained at the end of said method, in particular by avoiding false positive results (also called "false positives") and/or false negative results (also called "false negatives").

A "false positive" is a positive result reflecting the presence of one or more analytes to be detected in a sample, while said one or more analytes are not present in the sample and therefore should not have been detected.

A "false negative" is a negative result reflecting the absence of one or more analytes to be detected in a sample, while said one or more analytes were present in the sample and should have been detected.

The detected signal corresponding to the presence of an analyte at a dot allows to detect the presence of an analyte in a sample and/or to quantify said analyte in said sample.

The detected signal corresponding to the presence of an analyte at a dot is an electromagnetic radiation, in particular light emission.

The detected signal corresponding to the presence of an analyte at a dot is preferably a signal detected by luminescence, such as chemiluminescence, and/or a signal detected by fluorescence.

The fluorophore present in the dot or dots of a solid support can be used, inter alia, to control the quality of the dot or dots (in particular their presence, location and/or integrity) at the end of an analytical method, and/or to improve the sensitivity of detection of the analytes by defining a read gate of the signal corresponding to the analyte or analytes from the actual location of the dot or dots at the end of the analytical method. The use of a fluorophore in the dot or dots of a solid support thus also allows to secure the results of an analytical method performed on a dot or dots.

The use of a dye according to the invention thus makes it possible to improve (and therefore secure) the detection of a signal corresponding to the presence of an analyte in an analytical method by masking and/or absorbing, partially or entirely, unwanted light interference during the acquisition of a signal to be detected in the presence of a liquid phase. The improvement of the detection of the signal can be assessed by measuring the ratio of "detected signal to background noise."

Furthermore, the use of a dye in an analytical method according to the invention has the advantage of being able to use a solid support in which the walls of the compartment or compartments comprise or consist of a transparent material, this type of support being less expensive than those comprising or consisting of an opaque material.

A first object of the invention is thus to provide an analytical method, preferably a multiplex analytical method, allowing to improve the detection of a signal corresponding to the presence of an analyte, comprising the following steps:
a) providing a solid support comprising at least one compartment, said compartment comprising at least one dot for detection of an analyte,
b) contacting a sample to be analyzed with the dot or dots of said compartment of the solid support,
c) contacting at least one analyte detecting ligand with the dot or dots of said compartment, said analyte detecting ligand being coupled to a direct or indirect detection marker,
d) when said detection marker is an indirect marker, contacting a reporter of the indirect detection marker coupled to said detection ligand with the dot or dots of said compartment,
e) when the reporter used in step d) is coupled to an indirect marker, contacting a reporter of said indirect detection marker coupled to said reporter with the dot or dots of said compartment,
f) contacting at least one dye with the dot or dots of said compartment, said one or more dyes being in a liquid phase in contact with the dot or dots of said compartment, and
g) detecting a signal corresponding to the presence of an analyte at the dot or dots of said compartment, in the presence of the liquid phase comprising said one or more dyes.

A second object of the invention relates to the use of at least one dye for improving the detection of a signal corresponding to the presence of an analyte in an analytical method performed on a dot or dots, the improvement of the detection of the signal being characterized, for example, by a decrease in the intensity of the background noise.

Sample

The sample to be analyzed is preferably a biological sample.

The biological sample can be a biological fluid, such as a blood sample derived from blood (such as plasma or serum), urine, cerebrospinal fluid, saliva, or a tissue sample, such as a tissue obtained by biopsy, a cell, a set of cells, a plant extract, or combinations thereof.

A blood derivative means any product, in particular fluid, obtained from a blood sample.

The sample to be analyzed can also be a culture medium and/or culture supernatant.

Before being analyzed, the sample may undergo one or more pretreatment steps, such as dilution, centrifugation, thermal treatment, cell lysis (e.g., by one or more chaotropic agents, one or more reducing agents, and/or by heating), extraction, PCR reaction (Polymerase Chain Reaction), adding a non-marker-labeled detection ligand, or combinations thereof. The addition of a non-marker-labeled detection ligand is especially useful for the implementation of a neutralization test, which in itself is a test known to those skilled in the art.

The sample may also be a mixture of at least two samples which may be of the same nature or of different nature.

As an example of a mixture of samples of different nature, there may be mentioned a mixture of blood and serum, a mixture of blood and plasma, a mixture of serum and plasma, or a mixture of blood, serum and plasma.

A preferred sample of this invention is a sample or a mixture of samples of blood and/or blood derivative.

Analyte

An analyte to be detected in the sample can be any type of compound, natural or synthetic, that is desirably detected and/or quantified in a sample.

An analyte can for example be a protein, a peptide, a glycoprotein, a carbohydrate, a lipid, a cell, an organelle, a virus or a nucleic acid.

The cell may be an animal cell, a plant cell, a bacterial cell, a metazoan cell, a yeast cell, a fungal cell or a protozoan.

A nucleic acid refers to a polymer of nucleotides joined by phosphodiester linkages, such as a deoxyribonucleic acid (DNA), a ribonucleic acid (RNA) or an analogue thereof, such as phosphorothioates or thioesters, in single stranded or double stranded form.

An analyte or at least one of the analytes is for example selected from the group consisting of an antigen, an antibody, an antibody fragment, a hapten, a hormone, a hormone receptor, an enzyme or a nucleic acid.

An "antigen" is herein understood to mean a natural or synthetic molecule recognized by antibodies or cells of the immune system and capable of inducing an immune response. An antigen is for example a protein, peptide, glycoprotein, carbohydrate or lipid.

A "hapten" is herein understood to mean a low molecular weight molecule capable of being recognized by the immune system, but that is immunogenic only when coupled to a carrier molecule.

A "carrier molecule" (or "support molecule") in the present application is understood to mean a protein or carbohydrate carrier molecule.

A carrier molecule can be a polypeptide (particularly a protein or peptide), natural or non-natural (e.g., a recombinant protein or a synthetic peptide), a functionalized polymer (dextran type, polysaccharide, or polylysine), a mixed copolymer (in particular a copolymer of different amino acids, e.g. a copolymeric lysine-tyrosine), or an antibody (particularly a monoclonal antibody or a polyclonal antibody), for example an immunoglobulin (also referred to as Ig). An example of a carrier molecule is BSA (bovine serum albumin).

An analyte or at least one of the analytes is preferably a compound allowing to diagnose a condition of a subject, pathological or not, or to diagnose the risk of developing a condition, pathological or not. An example of a non-pathological condition is pregnancy.

The subject may be a human, a nonhuman animal or a plant. The non-human animal is preferably a mammal, such as a cat, dog, monkey, rabbit, mouse, rat.

The term "human" is used broadly and refers particularly to a male or female of any age, such as an infant, a child, a teenager, an adult or a senior.

When the analyte or at least one of the analytes is an antigen, it is preferably an antigen allowing to diagnose an infection, for example an infection caused by a virus, a bacterium, a fungus or a parasite.

When the analyte or at least one of the analytes is an antibody, it is preferably an antibody allowing to diagnose an infection, for example an infection caused by a virus, a bacterium, a fungus or a parasite.

Typically, there may be one or more antigens and/or one or more specific antibodies of:
- a virus, such as HIV (human immunodeficiency virus), in particular HIV-1 or HIV-2, HBV (hepatitis B virus), HCV (hepatitis C virus), HPV (human papillomavirus), HTLV (human T-lymphotropic virus), in particular HTLV-I or HTLV-II,
- a parasite, such as a parasite that can cause toxoplasmosis (*Toxoplasma gondii* in particular), malaria (in particular a parasite of the genus *Plasmodium*, for example *Plasmodium falciparum, Plasmodium vivax, Plasmodium ovale, Plasmodium malariae* or *Plasmodium knowlesi*) or Chagas disease (especially *Trypanosoma cruzi*), in a human or non-human animal, or
- a bacterium such as a bacterium capable of causing syphilis (*Treponema pallidum* in particular) or Lyme disease (particularly a bacterium of the genus *Borrelia*), in a human or non-human animal.

A "parasite" herein refers to a metazoan or protozoan parasiting an organism and causing a parasitic disease. A parasite within the meaning of the invention is thus neither a virus, nor a bacterium, nor a fungus.

The analyte or at least one of the analytes may also be a marker of a disease, such as a marker of cardiovascular disease or a marker of diabetes, a marker of disease progression, such as hepatitis, a marker of the progression of an infection caused by a virus, bacterium, fungus or parasite, a marker of resistance to a treatment, for example in antiviral treatment, an antibiotic treatment or treatment against cancer.

Several (e.g., two, three, four, five, six, seven, eight, nine, ten, eleven, twelve, thirteen, fourteen, fifteen, sixteen or more than sixteen) analytes as described in the present application can be detected simultaneously in a sample in a multiplex analytical method. This may allow to diagnose, in the same sample, one or more infection(s) or disease(s), the course of an infection or disease, a condition (disease or not), a risk of developing a condition (pathological or not) or a resistance marker to a treatment in a subject.

Analytes detected in the course of a multiplex analytical method can be of the same nature (for example only the antibodies or antigens only) or of a different nature (for example, at least one antigen and at least one antibody).

Capture Ligand

A capture ligand is a compound attached to a solid support at a dot.

At least one capture ligand is specific for an analyte to be detected in the sample.

A capture ligand may be an antibody, an antigen, a peptide, a carbohydrate, a lipid or a nucleic acid.

A capture ligand is preferably an antibody or antigen.

If a capture ligand is an antibody, it is for example a monoclonal antibody or a polyclonal antibody.

Detection Ligand

A detection ligand is intended to reveal the presence of a compound for which it is specific.

A detection ligand may be an antibody, an antigen, a peptide, a carbohydrate, a lipid or a nucleic acid.

A detection ligand is preferably an antibody or antigen.

If a detection ligand is an antibody, it is for example a monoclonal antibody or a polyclonal antibody.

A detection ligand is preferably a marker-labeled detection ligand, i.e., a ligand to which a detectable marker is covalently or non-covalently attached.

When a detection ligand is not marker-labeled, its detection can be obtained by using a marker-labeled antibody specific for said detection ligand.

At least one detection ligand is specific for an analyte to be detected in the sample.

A detection ligand may be the same as the capture ligand or to one of the capture ligands used, except for the possible presence of a detection marker, and/or bind to the compound for which it is specific in the same area as that bound by the capture ligand or one of the capture ligands. In this case, if said capture ligand and said detection ligand are antibodies, then it is a "homologous sandwich assay".

A capture ligand and the detection ligand or one of the detection ligands may be specific to distinct areas at the compound for which they are specific, so as to avoid a competition between the capture ligand and the detection ligand for the compound for which they are specific, due to steric hindrance. In this case, if said detection ligand and said capture ligand are antibodies, then it is a "heterologous sandwich assay".

In a preferred embodiment, a detection ligand and a capture ligand specific for the same compound do not bind to the same location on said compound. More preferably, said detection ligand binds to a region of said compound which is remote from the binding region with said capture ligand.

In another preferred embodiment, a detection ligand is identical to a capture ligand, with the exception of the possible presence of a detection marker, and/or binds to the compound for which it is specific in the same area as that bound by said capture ligand, when the compound for which it is specific is in the form of a complex having at least two identical binding areas.

Detection Marker

A detection marker may be a direct marker, or an indirect marker.

A direct marker is one in which the signal can be detected directly, i.e., without requiring the prior addition of a reporter.

A direct marker is, for example, selected from the group consisting of a fluorophore, a luminescent compound, fluorescent or luminescent nanoparticles.

A "luminescent" compound may be an electroluminescent compound, a thermoluminescent compound or a chemiluminescent compound. In a preferred embodiment, the luminescent compound is a chemiluminescent compound.

An example of a luminescent compound (more precisely of a thermoluminescent compound) that can be used as direct marker consists of silica nanoparticles comprising (for example added to or doped with) molecules of a dioxetane compound, especially the compound 1,2-dioxetane, or derivative of a dioxetane compound, for example, a derivative of 1,2-dioxetane.

An indirect marker is a marker whose detection signal beforehand requires the addition of a reporter (also referred to as first reporter) and, where said reporter is itself coupled to an indirect detection marker, the addition of a second reporter of the indirect detection marker coupled to said first reporter.

An indirect marker is, for example, selected from the group consisting of an enzyme, a ligand of a ligand-receptor pair, a receptor of a ligand-receptor pair, a hapten, an antigen and an antibody.

A ligand or a receptor of a ligand-receptor pair is, for example, biotin, a biotin analogue, avidin, streptavidin, neutravidin or digoxigenin.

A reporter is a substrate of an indirect marker or a molecule specifically binding to an indirect marker, said molecule itself being a direct or indirect marker or being itself coupled to a direct or indirect marker.

A substrate is, for example, the substrate of an enzyme.

A molecule specifically binding to an indirect marker is, for example, a ligand or receptor of a ligand-receptor pair, such as biotin, biotin analogue, avidin, streptavidin, neutravidin or digoxigenin.

A reporter of an enzyme is for example the substrate of said enzyme.

A reporter of a molecule capable of producing a luminescent compound is for example a substrate, an enzyme or a catalyst.

A reporter of biotin is for example avidin, streptavidin or neutravidin, preferably coupled to a direct marker or to an indirect marker, such as an enzyme.

Preferred indirect markers of the invention are biotin and an enzyme, preferably an enzyme producing a luminescent compound by reaction with a substrate.

An example of an enzyme is a peroxidase, such as horseradish peroxidase (HRP), luciferase or alkaline phosphatase.

A preferred reporter of the biotin according to the invention is streptavidin coupled to a peroxidase, preferably horseradish peroxidase.

For example, if the reporter (also referred to as the first reporter) of the indirect detection marker coupled to a detection ligand of an analyte is coupled to a peroxidase enzyme, it is necessary to add in a subsequent step the reporter (also referred to as the second reporter) of this peroxidase enzyme, i.e., a substrate of this enzyme, such as luminol, isoluminol and/or a derivative of luminol or isoluminol. In this case, the second reporter is a substrate.

Solid Support

The support or supports used for the implementation of an analytical method according to the invention are solid supports.

A solid support can be any material suitable for the implementation of an analytical method.

A solid support is for example a support based on a polymer or mixture of polymers. A suitable solid support of the invention is, for example, a support made of polystyrene, polypropylene, poly(meth)acrylate, polybutadiene, or combinations thereof.

A preferred solid support is made of polystyrene and/or polypropylene.

Another type of solid support suitable according to the invention is for example an inorganic solid support, such as glass.

A support may for example be in the form of a plate, a microplate, a slide or a membrane.

A solid support comprises at least one compartment, which is also called analysis area. The compartment or compartments of a solid support define the orientation of the solid support. The top of a solid support (also called upper surface of the solid support) is on the side of the compartment or compartments and thus on the side of the dot or dots. The bottom of a solid support (also called lower surface of a solid support) is the opposite surface.

According to a particular embodiment of the invention, a solid support comprises a single compartment.

Said single compartment can be a compartment comprising or consisting of a bottom and one or more walls.

Alternatively, said single compartment can be free of walls and be integrated with the solid support itself. The bottom of the compartment may then consist of the upper surface of the solid support.

An example of such a solid support comprising a single compartment (whether or not comprising one or more walls) is a slide or membrane.

According to another particular embodiment of the invention, a solid support, which may be for example a microplate, comprises at least two compartments.

When a solid support comprises at least two compartments, they are isolated from each other, so that they do not communicate with each other, i.e., so that the fluids (also called solutions) used in the implementation of an analytical method can not flow from one compartment to another during the analytical process.

Thus, a solution added in one compartment is not found in the other compartments. For example, the compartments comprise or consist of a bottom and one or more walls, said wall or walls insulating the compartments from each other so that they do not communicate with each other.

A solid support is preferably a microplate. In this case, an example of a compartment is a well. The microplate is typically a microplate of 96 wells or 384 wells.

In a particular embodiment, when a solid support comprises at least two compartments, they may also be isolated from each other, so that a signal emitted at one compartment is not, partly or entirely, detected in any other compartment. For this purpose, the wall or walls of the compartments can include or be made of an opaque material.

An "opaque material" herein means, in particular, a material not letting pass or substantially not letting pass the signal to be detected that corresponds to the presence of an analyte. "Substantially not letting pass the signal to be detected" means that the opaque material lets pass at most 20%, preferably at most 15%, more preferably at most 10%, even more preferably at most 5%, more particularly preferably at most 2%, at most 1% or at most 0.5% of the signal to be detected. An example of opaque material is a black material.

In another particular embodiment, when a solid support comprises at least two compartments, the wall or walls of the compartments comprise or consist of a transparent material.

In another particular embodiment, when a solid support comprises at least two compartments, the compartments may include at least one wall made of a transparent material and at least one wall made of an opaque material.

A "transparent material" means, in particular, a material letting pass at least 80% of a detecting signal corresponding to the presence of an analyte, preferably at least 85% of the signal to be detected, more preferably at least 90% of signal to be detected, more preferably at least 95% of the signal to be detected.

In a preferred embodiment, the bottom of the compartment or compartments of a solid support comprises or consists of a transparent material, in order to enable detection of the signal to be detected that corresponds to the presence of an analyte through the bottom of the compartment.

Examples of opaque material are colored glass, colored polystyrene, colored polyethylene, colored polypropylene and combinations thereof.

Examples of transparent material include glass, polystyrene, polymethylpentene, polycarbonate, acrylonitrile-butadiene-styrene, polymethyl methacrylate or combinations thereof.

Typically, at least one (e.g. one or two) compartment of a solid support is used per sample to be analyzed.

In a particular embodiment of the invention wherein a solid support (for example a slide or a membrane) comprises a single compartment, at least one (e.g. one or two) solid support is used per sample to be analyzed.

A compartment of a solid support used to analyze a sample comprises at least one dot, at least two dots, at least three dots, for example three dots, four or five dots, or at least six dots, preferably six dots, seven dots, eight dots, more preferably at least nine dots, such as nine dots, ten dots, eleven dots, twelve dots, thirteen dots, fourteen dots, fifteen dots, sixteen dots or more than sixteen dots.

A "dot" herein means an area on the surface of the bottom of a compartment of a solid support comprising at least one compound of interest. The compound or compounds of interest can be attached to the bottom surface of a compartment by non-covalent physicochemical interactions (e.g. of the weak bond type, and in particular ionic, van der Waals, hydrogen and/or hydrophobic) and/or by covalent bonds.

A dot may comprise, besides the compound(s) of interest, at least one polymer, in particular at least one polymer having hydrophilic groups, for example, at least one hydrogel.

"At least" in the present application means one or more, "several" meaning in particular two, three, four, five, six, seven, eight, nine, ten, eleven, twelve, thirteen, fourteen, fifteen, sixteen or more than sixteen.

A dot corresponds to a well-defined area, generally of small size, for example in the range of 0.0078 $mm^2$ to 5.309 $mm^2$, preferably from 0.196 $mm^2$ to 3.142 $mm^2$, more preferably from 0.503 $mm^2$ to 2.011 $mm^2$.

A dot can be of a discoidal or approximately discoidal shape, for example oval, especially when a solid support is a microplate or a slide.

Alternatively, a dot can be of a square or rectangular shape (in particular a strip), for example when the solid support is a membrane, or any other form.

The dots are obtained by techniques well known to the skilled person (see, for example, documents U.S. Pat. Nos. 7,470,547, 6,576,295, 5,916,524 and 5,743,960).

For example, a dot is obtained by depositing at least one drop of a solution containing a controlled amount of said compound(s) of interest at a specific location on the surface of the compartment.

When a dot comprises at least one polymer (e.g., at least one hydrogel), said dot can be obtained by depositing at least one drop of a solution containing a controlled amount of said compound(s) of interest at a specific location on the surface of the compartment on which said polymer was deposited beforehand.

A dot may also be obtained by in situ synthesis of said compound or compounds of interest at a specific location on the surface of the compartment. Said one or more compounds of interest are in this case referred to as "probes". It can be a nucleic acid or a peptide (see e.g. document U.S. Pat. No. 5,143,854).

The compound of interest can be, for example, a capture ligand, a carrier molecule coupled to an indirect marker, an indirect marker, or a fluorophore.

In a preferred embodiment, at least one dot of a compartment comprises at least one specific capture ligand of an analyte to be detected.

In an advantageous embodiment, at least one dot of a compartment, preferably all dots of a compartment, comprise at least two compounds of interest, one of these compounds of interest being a fluorophore. Said fluorophore is then used in particular to monitor the presence, location and/or integrity of the dots as a result of an analytical method, in particular a multiplex analytical method. For example, at least one dot of a compartment comprises at least one specific detection ligand of an analyte and at least one fluorophore.

In an advantageous embodiment, each compartment of a solid support includes the same number of dots. In addition, each compartment of a solid support may comprise the same number of dots and composition in dots.

In another advantageous embodiment, a support may comprise one or more compartments without a dot, or with a different number and/or composition of dots. A solid support can for example comprise at least two distinct groups (or types) of compartments, each of the distinct groups having a different number and/or composition of dots.

A compartment usually includes at least one dot per analyte to be detected, each analyte may for example correspond to an infection or disease to be detected, to the course of an infection or disease, to a condition (pathological or not) of a subject, to a risk of developing a condition (pathological or not) or to a marker of resistance to treatment. Several dots of one compartment can also be intended for analysis of the same analyte.

A compartment therefore comprises at least one dot for detection of an analyte, preferably at least two dots for the detection of an analyte.

The same dot may comprise several different capture ligands (e.g. several antibodies and/or antigens) which are for example specific for the same infection or disease to be detected (specific in particular of the same virus, the same bacterium or the same parasite), or specific for the same course of an infection or disease, of the same condition (pathological or not) of a subject, the same risk of developing a condition (pathological or not), or the same marker of resistance to treatment.

In an advantageous embodiment, a compartment comprises at least one control dot allowing to validate at least one step of an analytical method, particularly a multiplex analytical method.

Signal Detection

The detection of the signal depends on the type of marker used.

The detected signal is electromagnetic radiation.

The electromagnetic radiation can be light, for example ultraviolet radiation, visible light or infrared radiation.

The ultraviolet radiation is electromagnetic radiation of a wavelength of 10 to 380 nm. Visible light is electromagnetic radiation of a wavelength of from 380 nm to 780 nm. Infrared radiation is electromagnetic radiation of a wavelength of 780 nm to 1 mm.

The terms "signal detection" and "signal acquisition" are synonymous here.

"Detection of the signal" means, in particular, the detection of a signal corresponding to the presence of an analyte or the detection of a signal corresponding to a process control.

The skilled person knows how to detect a signal at a dot based on the detection markers employed. The signal is for example detected by means of a camera that captures the image of the bottom of the solid support.

Detecting the signal generally comprises a measure of signal strength, for example expressed in RLU (Relative Light Unit).

The signal emitted by a fluorophore type direct marker can be read directly by fluorescence after excitation by light energy.

Indeed, a fluorophore, also called fluorochrome or fluorescent molecule, is a chemical substance capable of emitting fluorescent light upon excitation with light energy.

As stated previously, an indirect marker, for example of the enzyme or biotin type, requires the addition of a reporter, the reporter may be coupled to a direct or indirect marker. If a reporter is itself coupled to an indirect marker, for example an enzyme, it is necessary to add in a subsequent step a reporter of this indirect marker, for example the substrate of this enzyme.

In the context of the present invention, the dye or dyes employed must be present during the detection of the signal, and signal detection is performed in the presence of a liquid phase.

Using a dye according to the invention, it is possible to reduce the background noise and in particular to improve the ratio of "detected signal to background noise," by detecting the signal corresponding to the presence of an analyte and emitted from dots through the bottom of the solid support.

In a preferred embodiment, the signal detected in the analytical method according to the invention is a chemiluminescent signal emitted by a chemiluminescent compound.

Chemiluminescence is a chemical reaction which results in the production of light. A reaction of this type is the redox reaction of luminol (3-aminophthalhydrazide, also called 5-amino-2,3-dihydrophthalazine-1,4-dione, empirical formula $C_8H_7N_3O_2$), of isoluminol or a luminol or isoluminol derivative with an oxidant, for example hydrogen peroxide or any hydroxide. During a chemiluminescent reaction, the molecule produced by the reaction is in an excited state: it is the chemiluminescent compound. It is the return of this chemiluminescent compound to the ground state which causes the emission of light.

In a preferred embodiment, the signal detected by chemiluminescence is emitted by the reaction of a peroxidase enzyme with its substrate, for example, luminol, isoluminol (also called 4-aminophthalhydrazide) and/or a derivative of luminol or isoluminol. This reaction also requires the presence of an oxidant and, if necessary, an electron mediator.

A derivative of luminol or isoluminol is preferably a molecule obtained from luminol or isoluminol by any possible modifications (for example, chemical and/or enzymatic ones). A derivative of luminol or isoluminol is particularly a peroxidase enzyme substrate, the reaction of said peroxidase enzyme with said luminol or isoluminol derivative allowing for the production of a chemiluminescent compound.

A derivative of isoluminol may be e.g. aminoethylisoluminol (or AEI), aminoethylethylisoluminol (or AEEI), aminobutylisoluminol (or ABI), aminobutylethylisoluminol (or ABEI), aminopentylethylisoluminol (or APEI), aminohexylisoluminol (or AHI), aminohexylethylisoluminol (or AHEI), aminooctylmethylisoluminol (or AOMI), or aminooctylethylisoluminol (or AOEI), as described in the publication Dodeigne C. et al. (2000), Talanta 51, 415-439, "Chemiluminescence as diagnostic tool. A review".

According to another particular embodiment, the signal detected by chemiluminescence is generated by an enzymatic or chemical reaction with a substrate selected from an acridine, coelenterazine, dioxetane or peroxyoxalic compound, or a derivative thereof, especially a compound described in publication Dodeigne C. et al. (2000), Talanta 51, 415-439, "Chemiluminescence as diagnostic tool. A review".

An electron mediator is, for example, sodium 3-(10'-phenothiazinyl)propane-1-sulfonate, p-iodophenol, p-iodophenylboronic acid, 4-(phenothiazine-10-yl)butane-1-sulfonic acid, or combinations thereof.

An oxidant is, for example, a peroxide, e.g. hydrogen peroxide, or sodium perborate.

The signal from the reaction of a peroxidase enzyme with luminol, isoluminol and/or a derivative of luminol or isoluminol is read at a wavelength of 375 nm to 580 nm, for example 425 nm.

The detected signal is preferably expressed in RLU (Relative Light Unit).

The peroxidase enzyme may be coupled to a detection ligand, for example a detection ligand specific for an analyte, or to a reporter of an indirect detection marker, such as streptavidin.

Generally, the chemiluminescence reaction is effected by means of a kit comprising at least two solutions.

The first solution comprises the peroxidase substrate, such as luminol, isoluminol and/or a derivative of luminol or isoluminol, and an electron mediator; the second solution comprises an oxidant. For example, it is possible to use the kit "Immun-Star Western C" (Bio-Rad, USA), "ELISTAR ETA C Ultra ELISA" (Cyanagen, Italy), "Supersignal West Pico" (Thermo Scientific, USA), "Chemiluminescent Sensitive+HRP" (Surmodics, USA).

Fluorophore Used as a Control

In an advantageous embodiment, the one or more dots of at least one compartment of a solid support include a fluorophore used as a control.

The fluorophore used as a control preferably does not interfere, or interferes little, with the signal corresponding to the presence of an analyte, for example with the signal emitted by a chemiluminescent compound.

For example, when the signal corresponding to the presence of an analyte is a chemiluminescent compound obtained from luminol, isoluminol and/or a derivative of luminol or isoluminol, the fluorophore used as a control preferably emits no light around 425 nm, in particular from 400 nm to 550 nm, preferably 375 nm to 550 nm, more preferably from 350 nm to 580 nm. It may, for example, emit light only at wavelengths shorter than (or less than or equal to) 400 nm, 390 nm, 380 nm, 375 nm, 370 nm, 360 nm or 350 nm, or only at wavelengths longer than (or greater than or equal to) 550 nm, 560 nm, 570 nm, 580 nm, 590 nm or 600 nm.

A fluorophore used as a control is, for example, selected from the group consisting of a coumarin, rhodamine, carbopyronine, oxazine, benzpyrylium, phycoerythrin and derivatives thereof. Said fluorophore is optionally coupled to a carrier molecule, for example a protein, such as BSA.

A fluorophore used as a control is, for example, selected from the group consisting of a coumarin, rhodamine, carbopyronine, oxazine, B-phycoerythrin, a benzpyrylium derivative, and derivatives thereof.

A fluorophore used as a control is preferably selected from the group consisting of a carbopyronine, carbopyronine derivative, an oxazine, an oxazine derivative, a benzopyrylium derivative, and phycoerythrin.

A more preferred fluorophore for use as a control is selected from the group consisting of a carbopyronine, a benzopyrylium derivative and a phycoerythrin.

Alternatively, a preferred fluorophore for use as a control can be selected from the group consisting of a derivative of carbopyronine, a derivative of benzopyrylium, and a phycoerythrin.

A preferred fluorophore that can be used in the dots as a control is, for example, a carbopyronine comprising the following basic structure:

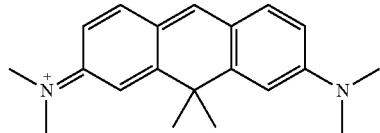

For example, there may be mentioned the carbopyronine Atto 633 sold by AttoTec, and its derivatives, in particular an amino derivative of Atto 633.

Another example of a preferred fluorophore that can be used in the dots as a control is the fluorophore sold by Dyomics company under the name "Dye 634" (in a form coupled to a carrier molecule, such as BSA) whose formula is as follows:

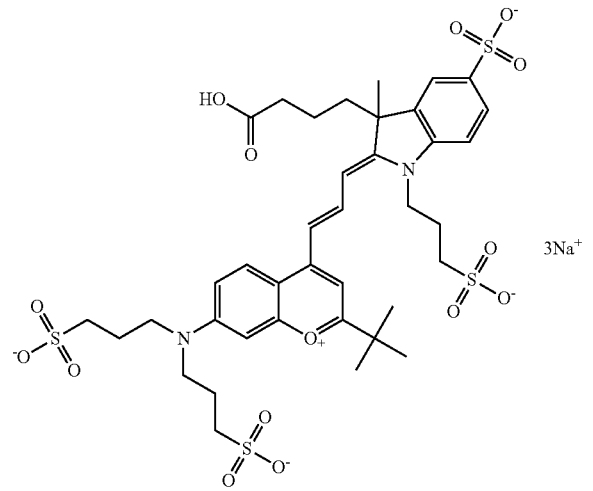

This is a benzpyrylium derivative.

Dye 634 can also be used in its amine form (Dye-634 amine) in the dots as a control. It can then be used while coupled or not to a carrier molecule and in particular to BSA.

Yet another example of a preferred benzopyrylium derivative fluorophore that can be used in the dots as a control is the amino derivative of Dye 630, Dye 630 having the following formula:

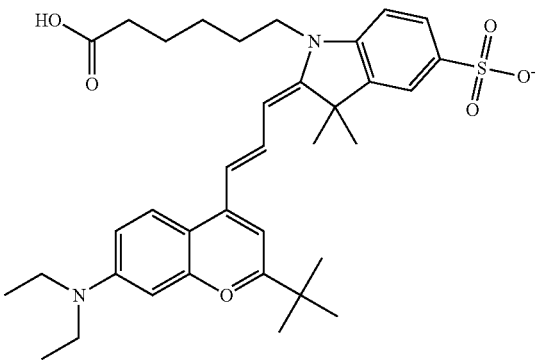

The amine derivative of Dye 630 can be used while coupled or not coupled to a carrier molecule and in particular to BSA.

Dye

The term "dye" here denotes a soluble compound that absorbs light in a range of wavelengths covering partially or entirely the emission wavelength range of the signal that it is desired to reduce (partially or entirely), i.e., of the signal causing the light interference.

When a luminescent compound, for example, a chemiluminescent compound, is used in an analytical method for detecting the presence of an analyte, a dye according to the invention preferably absorbs the light in a range of wavelengths covering entirely the emission wavelength range of said luminescent compound.

Typically, for a development system using the reaction of peroxidase on luminol, isoluminol and/or a derivative of luminol or isoluminol, the dye according to the invention preferably absorbs a range of wavelengths of from 375 nm to 580 nm.

When a fluorophore is used in an analytical method for detecting the presence of an analyte in a sample and optionally quantifying an analyte in a sample, the dye used is compatible with the detection of the signal emitted by said fluorophore. Thus, the dye used does not absorb light in a range of wavelengths corresponding to the range of the excitation and/or emission wavelengths of said fluorophore and, preferably, do not diffuse light corresponding to the range of excitation and/or emission wavelengths of said fluorophore.

In a preferred embodiment, the dye or dyes are not fluorescent in the red, i.e., they do not emit light at wavelengths ranging from 620 to 780 nm when excited by any light, in particular in basic medium.

For example, a preferred dye according to the invention does not absorb at 657 nm and, in particular, does not absorb between 620 and 800 nm, between 610 and 850 nm or between 600 and 900 nm or between 580 and 950 nm, and is itself not fluorescent.

Surprisingly, the dye according to the invention absorbs the signal causing the light interference, without interfering, or interfering little, with the signal to be detected, for example, by not interfering, or interfering little, with the light emitted by the chemiluminescent compound obtained from the reaction of a peroxidase enzyme with luminol, isoluminol and/or a derivative of luminol or isoluminol locally at the dots.

The term "compound X does not interfere or interferes little with a signal" herein means that the signal strength in the presence of compound X is reduced at most by 20%, preferably at most by 15%, even more preferably at most by 10%, relative to the intensity measured in the absence of said one or more dyes.

Furthermore, the dye or dyes according to the invention do not induce energy transfer with the chemiluminescent compound, as can be observed with fluorescein, which can pass into an activated state and emit at a wavelength higher than the emission wavelength of the chemiluminescent product produced by reacting a peroxidase enzyme with its substrate (e.g., luminol, isoluminol and/or a luminol derivative or isoluminol).

In an advantageous embodiment, a dye according to the invention further enables detection of the signal emitted by a fluorophore present as a control in the dots. Such a dye is for example obtained or obtainable by the selection method of such a dye as defined below under "method for selecting a dye further allowing detection of the signal emitted by a fluorophore present in the dots or as a control".

A dye according to the invention is, for example, selected from the group consisting of tartrazine, quinoline yellow, naphthol Yellow S, curcumin, riboflavin and riboflavin 5'-phosphate.

Thus, surprisingly, the dye or dyes of the invention thus make it possible to partially or totally reduce the light interference from a chemiluminescent compound, without interfering, or with little interfering, with the signal to be detected by chemiluminescence and, where appropriate, allowing to detect the fluorescence emitted by a fluorophore present in the dots as a control.

The inventors have shown that the use of a single and unique dye, especially tartrazine, allows to improve (and thus secure) the detection of the signal in an analytical method performed on dots, in particular of a multiplex analytical method, and this without interfering with the signal emitted by a fluorophore possibly present in the dots.

Those skilled in the art can readily determine the optimum amount of dye(s) for use in an analytical method performed on dots, in particular a multiplex analytical method, for improving the desired detection of signal, for example by testing several concentrations of the dye(s).

A Method of Selecting a Dye Further Allowing Detection of the Signal Emitted by a Fluorophore Present in the Dot or Dots as a Control The present invention also relates to a method of selecting a dye further allowing the detection of the signal emitted by a fluorophore present in the dot or dots of a solid support, said method comprising the following steps:

a) contacting a liquid phase comprising a dye to be tested or a mixture of dyes to be tested with the dot or dots of a compartment of a solid support, at least one of the dots of said compartment comprising a fluorophore,
b) detecting a signal emitted by said fluorophore in the presence of said liquid phase comprising said dye to be tested or said mixture of dyes to be tested, and
c) selecting a dye or mixture of dyes in the presence of which the signal detected in step b) makes it possible to locate the dot or dots comprising said fluorophore.

The dye to be tested or included in the mixture to be tested is a soluble compound that absorbs light in a range of wavelengths covering partially or wholly the emission wavelength range of the signal that it is desired to be reduced (partially or fully), i.e., of the signal causing the light interference.

Step a) is performed for each dye or mixture of dyes to be tested.

In step a), the same dye to be tested or mixture of dyes to be tested may be added in several compartments, for example at different concentrations in order to test different concentrations of said dye or mixture of dyes.

A different compartment is used for each different dye to be tested or mixture of dyes to be tested.

Absorbing Composition Based on at Least One Dye

In an advantageous embodiment, the dye as defined above under "dye" is provided in the form of an absorbent composition.

An absorbent composition according to the invention is an aqueous solution comprising at least one dye.

A preferred absorbent composition comprises only one dye. For example, a preferred absorbent composition comprises tartrazine as the only dye.

The absorbent composition according to the invention may comprise 100 μg/ml to 3000 μg/ml of dye, preferably 200 μg/ml to 2500 μg/ml of dye, more preferably from 250 μg/ml to 2000 μg/ml of dye, for example 250 μg/ml to 500 μg/ml, or 1000 μg/ml to 2000 μg/ml. For example, the absorbent composition may comprise 250 μg/ml, 500 μg/ml, 1000 μg/ml, or 2000 μg/ml of dye.

The absorbent composition according to the invention may comprise from 0.187 mM to 5.614 mM dye, preferably 0.374 mM to 4.678 mM dye, more preferably from 0.468 mM to 3.743 mM dye, e.g., 0.468 mM to 0.936 mM or 1.871 mM to 3,743 mM. For example, the absorbent composition may comprise 0.468 mM, 0.936 mM, 1.871 mM or 3.743 mM of dye.

Advantageously, the absorbent composition comprises a dye or at least one dye and at least one compound involved in the production of a chemiluminescent compound. Such an absorbent composition has the advantage of being stable over time.

The term "stable over time" means that, during the implementation of the same method of analysis, the signal detected using an absorbent composition to Day 0 is substantially identical to the signal detected using said absorbing composition after conservation of said absorbent composition for at least one month at 4° C. and/or 37° C., preferably for at least 3 months at 4° C., for example 3 months, 6 months, one year, or two years at 4° C.

The term "substantially identical" means that the detected signal varies at most 40%, preferably at most 30%, more preferably at most 20%.

The absorbent composition may be mixed with one or more compositions and/or one or more compounds used in the context of an analytical method, in particular used in the development step or steps.

In an advantageous embodiment, the absorbent composition of the invention further comprises at least one compound selected from the group consisting of luminol, isoluminol, a derivative of luminol or isoluminol, an electron mediator and an oxidant.

The luminol, isoluminol, derivative of luminol or isoluminol, the peroxidase enzyme, the electron mediator and the oxidant are in particular as defined above.

A preferred absorbent composition comprises at least one dye, for example tartrazine, at least one compound selected from luminol, isoluminol or a derivative of luminol or isoluminol, and optionally an electron mediator.

Another preferred absorbent composition comprises at least one dye, for example tartrazine, and at least one oxidant, for example a peroxide.

The absorbent compositions according to the invention advantageously comprise at least one solvent.

A solvent used in the absorbing composition is preferably compatible with an enzymatic reaction leading to the production of a luminescent compound, such as reaction of the peroxidase with luminol, isoluminol and/or a derivative of luminol or isoluminol.

A preferred solvent for use in the absorbent composition is water.

Another example of a preferred absorbent composition comprises at least one dye, for example tartrazine, and does not include luminol, isoluminol, a derivative of luminol or isoluminol, electron mediator or oxidant. For example, such an absorbent composition comprises or consists of at least one dye, for example a single dye, and a solvent, for example water.

Improvement of Signal Detection

The use of at least one dye as defined above or an absorbent composition comprising it as defined above allows to improve (and thus secure) the detection of the signal in an analytical method performed on dot(s), preferably a multiplex analytical method performed on dots, particularly when detecting the signal is performed in the presence of a liquid phase.

"Improving the signal detection" means particularly the reduction of background noise, more particularly the improvement of the ratio of "detected signal to background noise", in the presence of at least one dye or of the absorbing composition comprising it, relative to the ratio of "detected signal to background noise" obtained in their absence.

The "detected signal" for evaluating the improvement of the ratio of "detected signal to background noise" is, for example, the signal intensity measured at a given dot (i.e., where said dot is located) in the presence of an analyte to be detected in a sample or measured at a given dot (i.e., where said dot is located) in the presence of a known amount of an analyte to be detected.

Preferably, the "detected signal" for evaluating the improvement of the ratio of "detected signal to background noise" is the intensity of the signal measured at a given dot (i.e., where said dot is located) in presence of an analyte present in an amount which induces, in the absence of a dye, light interference, such as a light arc, a twin dot and/or a luminous veil.

The signal intensity measured at a dot is usually expressed in RLU (relative light units).

The skilled person knows how to detect the signal at a dot (i.e., where said dot is located), depending on the detection marker or markers used, in particular by means of a camera which is advantageously located below the solid support.

The "background noise" is the light intensity measured at the areas of the bottom of a compartment of a solid support that do not include dots.

The background noise is usually expressed in RLU (relative light units).

An improvement in the ratio of "detected signal to background noise" exists if the ratio of "detected signal to background noise" is increased, for example by increasing the detected signal and reducing the background noise, or by reducing the detected signal and even more greatly reducing the background noise.

The use of a dye according to the invention allows, preferably, an increase in the ratio of "detected signal to background noise", in the presence of the dye or dyes as compared to in the absence of the dye or dyes, of at least 5%, preferably at least 10%, more preferably at least 15%, more preferably at least 20%, still more preferably at least 25%, such as at least 30%, or at least 40%.

The present invention is particularly suitable for an analytical method performed on dot(s), in particular a multiplex analytical method performed on dots based on a development by chemiluminescence. Indeed, in order that the signal emitted by chemiluminescence allows detection of the interaction of capture ligand/analyte/detection ligand by a signal amplification, it is necessary for the enzymatic reaction to proceed upon detection of the signal, and therefore that the enzyme substrate is present in a liquid phase at the dots, at the time of signal detection.

In the context of the present invention, the dye, for example provided in the form of an absorbent composition, must be present at the time of signal detection.

The dye may be added before, simultaneously or after the addition of one or more of the compounds required for the chemiluminescent reaction. In all cases, the dye must be present at the time of signal acquisition.

The compounds required for chemiluminescence reaction are generally an enzyme (e.g., a peroxidase enzyme), a substrate for the enzyme (e.g., luminol, isoluminol and/or a derivative of luminol or isoluminol), optionally at least one further compound, such as an oxidant (e.g., peroxide) and/or an electron mediator (e.g., sodium 3-(10'-phenothiazinyl)propane-1-sulfonate).

Method for Improving the Detection of a Signal

In particular, the present invention relates to an analytical method, preferably a multiplex analytical method, allowing to improve (and thus secure) the detection of a signal corresponding to the presence of an analyte, said method comprising or consisting in the following steps:

a) providing a solid support comprising at least one compartment, said compartment comprising at least one dot provided for the detection of an analyte, b) contacting a sample to be analyzed with the dot or dots of said compartment, c) contacting at least one analyte detecting ligand with the dot or dots of said compartment, said analyte detecting ligand being coupled to a direct or indirect detection marker, d) when said detection marker is an indirect marker, contacting a reporter of the indirect detection marker coupled to said detection ligand with the dot or dots of said compartment, e) when the reporter used in step d) is coupled to an indirect marker, contacting a reporter of said indirect detection marker coupled to said reporter with the dot or dots of said compartment, f) contacting at least one dye with the dot or dots of said compartment, said one or more dyes being in a liquid phase in contact with the dot or dots of said compartment, and g) detecting a signal corresponding to the presence of an analyte at the dot or dots of said compartment, in the presence of a liquid phase comprising said one or more dyes.

The method according to the invention preferably comprises, first step a); and then steps b) and c), which can be performed in this order, or step c) before step b), or steps b) and c) simultaneously; then step d); then steps e) and f), which can be performed in this order, or step f) before step e), or steps e) and f) simultaneously; then step g).

In a preferred embodiment, step f) is performed simultaneously with step e).

No washing step is performed between step f) and step g) (whether step e) is performed before, after, or simultaneously with step f)), so that the dye is present at the time of signal detection.

When step c) is performed before step b), there is no washing step between step c) and step b).

The term "contacting a compound X with the dot or dots of a compartment" in particular means that the compound X is added to a compartment comprising said dot or dots, said compartment preferably being intended for analyzing a sample, and said compound X is preferably provided in the form of a composition comprising it, such as a solution, dispersion or suspension.

When at least two compounds are to be contacted with the dot or dots of a compartment during the same step and/or when at least two of steps b) to f) are carried out simultaneously, said compounds can be contacted with said dot or dots separately, i.e., provided in the form of separate compositions (in particular in the form of separate solutions, dispersions or suspensions); alternatively, said compounds or some of said compounds can be used in the presence of the dot or dots of a compartment in the form of one or more mixtures thereof.

The different compounds are contacted with the dots of at least one compartment for a certain period, for example from 1 second to 2 hours, preferably 1 minute to 1 hour, more preferably 5 minutes to 50 minutes, even more preferably from 10 minutes to 40 minutes.

The skilled person knows how to determine the appropriate temperature for each incubation step. The temperature of incubation may be for example 4° C., a temperature of 19° C. to 24° C., 37° C. or 40° C.

The different components used in the course of steps b), c), d) and e) are well known to those skilled in the art. They allow for example the formation of antigen-antibody and marker-reporter complexes.

The method further comprises one or more washing steps allowing to remove compounds not bound to the dots, or different compounds directly or indirectly bound to the dots.

Typically, a washing step consists of at least one cycle, preferably at least two cycles, more preferably 3 to 6 cycles, of distribution (e.g., a volume of 400 µl) and aspiration of a wash solution in each compartment used.

Steps b) to g) are in particular carried out for each compartment of a solid support comprising at least one dot intended for the detection of an analyte, in which a sample is analyzed.

Step a) consists in providing a solid support comprising at least one compartment, said compartment comprising at least one dot intended for the detection of an analyte, preferably at least two dots intended for the detection of an analyte.

Step a) means in particular that the analytical method is implemented by means of said solid support, i.e., using said solid support.

A solid support is in particular as defined above in the "Solid support" section.

In an advantageous embodiment, a solid support comprises at least one compartment of which at least one dot includes a fluorophore as a test of the dot or dots; preferably, a solid support comprises at least one compartment whose dots comprise a fluorophore as a control of the dots.

In step b), a sample to be analyzed is contacted with the dot or dots of a compartment of the solid support.

The sample to be analyzed and the analyte or analytes to be detected are in particular such as defined above in the "Sample" and "Analyte" sections.

In step c), at least a detection ligand of an analyte is contacted with the dot or dots of said compartment, said detection ligand of an analyte being coupled to a direct or indirect detection marker.

The detection ligand of an analyte is in particular as defined above.

In a preferred embodiment, a detection ligand for an analyte is coupled to an indirect detection marker selected from the group consisting of biotin, avidin, streptavidin and neutravidin.

When the detection marker is an indirect marker, the method comprises a step d) comprising or consisting of contacting a reporter (also known as first reporter) of said indirect detection marker coupled to said detection ligand with the dot or dots of said compartment, said reporter being itself coupled to a direct or indirect marker.

In a preferred embodiment, a reporter of the indirect detection marker coupled to a detection ligand of an analyte is selected from the group consisting of biotin, avidin, streptavidin and neutravidin.

For example, a detection ligand of an analyte is coupled to biotin, and the reporter of biotin is streptavidin coupled to a direct or indirect detection marker.

If the reporter (i.e., the first reporter) used in step d) is coupled to an indirect marker, the method further comprises a step e) consisting in contacting a reporter (i.e., a second reporter) of the indirect detection marker coupled to said reporter with the dot or dots of said compartment.

For example, a detection ligand of an analyte is coupled to biotin, and the reporter of biotin is streptavidin coupled to an enzyme. The reporter of the enzyme (i.e., the second reporter) is then the substrate of that enzyme.

In step f), at least one dye is contacted with the dot or dots of said compartment.

The dye is especially as defined above in the "Dye" section.

The dye is, for example, selected from the group consisting of tartrazine, quinoline yellow, Naphthol Yellow S, curcumin, riboflavin and riboflavin 5'-phosphate.

The dye may be provided in the form of an absorbing composition as defined above in the "Absorbing composition" section.

In an advantageous embodiment, the dye is provided in the form of an absorbent composition comprising at least one compound selected from the group consisting of luminol, isoluminol, a derivative of luminol or isoluminol, a mediator of electrons and an oxidant.

When the absorbent composition further comprises at least one compound selected from the group consisting of luminol, isoluminol, a derivative of luminol or isoluminol, an electron mediator and an oxidant, the steps e) and f) are performed simultaneously.

At the end of step f), the dye or dyes are included in a liquid phase in contact with the dot or dots of said compartment.

"Liquid phase contacting the dot or dots of said compartment" here means that a liquid composition is present in said compartment. Said composition may for example be a solution, dispersion or suspension.

The liquid phase in step f) may comprise or consist of an absorbent composition according to the invention, especially depending on whether step f) is performed before or after step e).

For example, when step f) is performed before step e) and step f) is preceded by at least one washing step, the liquid phase in step e) may consist of an absorbent composition.

When step f) is performed simultaneously with or after step e), the liquid phase in step e) may comprise the absorbent composition.

The step g) comprises detecting a signal corresponding to the presence of an analyte at the dot or dots of said compartment, the detection of said signal being conducted in the presence of the liquid phase comprising said one or more dyes.

The liquid phase in step g) may be identical to the liquid phase of step f), especially when step f) is performed after step e).

The liquid phase in step g) may be different from the liquid phase of step f), especially when step f) is performed before step e).

When the dye is provided in the form of an absorbent composition, the liquid phase in step g) comprises or consists of said absorbing composition.

When several different detection markers are used in the analytical method for the detection of the analyte or analytes, step g) comprises detecting as many different signals as detection markers used.

The signal detected in step g) corresponding to the presence of an analyte is, for example, the signal emitted by a luminescent compound, preferably a chemiluminescent compound, and/or the signal emitted by a fluorophore.

Preferably, the signal detected in step g) corresponding to the presence of an analyte is the signal emitted by a chemiluminescent compound.

Thus, step g) comprises at least the detection of a signal emitted at the dot or dots of said compartment which corresponds to the presence of an analyte, and the signal corresponding to the presence of an analyte is preferably emitted by a chemiluminescent compound.

Also, step g) can advantageously include the detection of a signal emitted by a fluorophore present as a control in one, several or all the dots of at least one compartment of the solid support.

The skilled person knows how to measure the emitted signal, for example by a luminescent compound or a fluorophore, depending on the nature of said luminescent compound or of said fluorophore.

The signal is preferably detected in step g) through the bottom of the solid support.

Signal detection preferably comprises a measurement of the intensity of the signal emitted at the dot or dots, said measurement being preferably carried out from below the solid support, i.e., at the lower surface of the solid support.

Signal detection is carried out in particular by means of a camera capturing the image of the bottom of the solid support. The measured signal is thus the signal passing through the solid support in the direction of the bottom surface of said solid support.

The camera can, for example, be directed towards the bottom of the solid support, or may capture the image of the bottom of the solid support by means of an optical system (which may for example comprise or consist of one or more mirrors, a prism and/or one or more lenses).

Measuring the intensity of the signal emitted by a fluorophore requires the one or more compartments to be illuminated, preferably from below the solid support, with a light corresponding to the excitation spectrum of the fluorophore.

The method of the invention as defined above thus allows to improve the detection of a signal corresponding to the presence of an analyte in an analytical method performed on dot(s), particularly when detecting the signal is performed in the presence of a liquid phase.

The improvement of the signal detection comprises or consists of a reduction of the background noise, preferably an increase of the ratio of "detected signal to background noise."

The ratio of "detected signal to background noise" is in particular such as defined above.

A preferred method allowing to improve the detection of a signal corresponding to the presence of an analyte in an analytical method, particularly a multiplex analytical method, is a method as defined above comprising the following steps:

a) providing a solid support comprising at least one compartment, said compartment comprising at least one dot intended for the detection of an analyte, said dot comprising a capture ligand of said analyte and preferably a fluorophore, b) contacting a sample to be analyzed with the dot or dots of said compartment, c) contacting at least one detection ligand of an analyte with the dot or dots of said compartment, said detection ligand of an analyte being coupled to an indirect detection marker, preferably biotin, d) contacting a reporter of the indirect detection marker coupled to said detection ligand, preferably streptavidin, with the dot or dots of said compartment, e) if the reporter used in step d) is coupled to a peroxidase enzyme, contacting a substrate of said enzyme, for example, luminol, isoluminol and/or a derivative of luminol or isoluminol, with the dot or dots of said compartment, e1) if the reporter used in step d) is coupled to a peroxidase enzyme, contacting at least one antioxidant, for example peroxide, and optionally at least one electron mediator, e.g., sodium 3-(10'-phenothiazinyl)propane 1-sulfonate with the dot or dots of said compartment, wherein said step e1) can be carried out before step e), after step e), or simultaneously with step e), f) contacting at least one dye, preferably tartrazine, with the dot or dots of said compartment, said one or more dyes being present in a liquid phase in contact with the dot or dots of said compartment, wherein step f) can be performed before or after step e), before or after step e1), or simultaneously with step e) and/or step e1), and g) detecting a signal corresponding to the presence of an analyte at the dot or dots of said compartment, in the presence of the liquid phase comprising said one or more dyes.

Use of at Least One Dye to Improve Signal Detection

The present invention particularly relates to the use of at least one dye to improve (and thus secure) the detection of a signal corresponding to the presence of an analyte in an analytical method on a solid support comprising at least one dot, in particular in a multiplex analytical method.

The solid support is in particular as defined above in the "Solid support" section. The solid support comprises in particular at least one compartment, said compartment comprising at least one dot intended for the detection of an analyte, preferably at least two dots intended for the detection of an analyte.

The dye is especially as defined above in the "Dye" section. The dye is, for example, selected from the group consisting of tartrazine, quinoline yellow, Naphthol Yellow S, curcumin, riboflavin and riboflavin 5'-phosphate.

The present invention particularly relates to the use as defined above, characterized in that the dye is tartrazine.

The dye may be provided in the form of an absorbing composition as defined above in the "Absorbing composition" section.

In a more preferred embodiment, the present invention relates to the use of tartrazine to improve the detection of a signal corresponding to the presence of an analyte in an analytical method performed on dot(s), particularly in a multiplex analytical method performed on dots.

The present invention more particularly relates to the use as defined above, characterized in that the detection of a signal corresponding to the presence of an analyte is performed in the presence of a liquid phase.

The signal detection preferably comprises a measurement of the intensity of the signal emitted at the dot or dots, said measurement being preferably carried out at the bottom surface of the solid support. Signal detection is carried out in particular by means of a camera capturing the image of the bottom of the solid support. As indicated above, the camera can, for example, be directed towards the bottom of the solid support, or may capture the image of the bottom of the solid support by means of an optical system (which may for example comprise or consist of one or more mirrors, a prism and/or one or more lenses).

The present invention particularly relates to the use as defined above, characterized in that the ratio of detected signal to background noise is increased.

The ratio of "signal detected to background noise" is in particular such as defined above.

The present invention preferably relates to the use as defined above, characterized in that the signal corresponding to the presence of an analyte is a signal emitted by a chemiluminescent compound and/or a fluorophore.

The present invention also relates to the use as defined above wherein the analytical method is implemented by means of a solid support as defined above, in particular of a solid support comprising at least one compartment of which at least one dot comprises a fluorophore as a control of the dots, preferably a solid support comprising at least one compartment of which the dots comprise a fluorophore as a control of the dots.

Other features and advantages of the invention will become clearer from the following examples, given for illustrative and not limiting purposes. These examples and figures illustrate the invention without limiting its scope.

FIGURES

FIG. 1: Schematic cross-section of a well of a microplate. Three real dots are shown on the bottom of the well which is made of a transparent film. The hollow arrows pointing down show the really useful emission that starts towards the camera. The solid arrows represent the light path in the well. These arrows illustrate the presence of bright artifacts originating in the scattering of light in the liquid medium, reflections on the wall of the well and at the liquid/air interface and at the meniscus.

Figure 2:
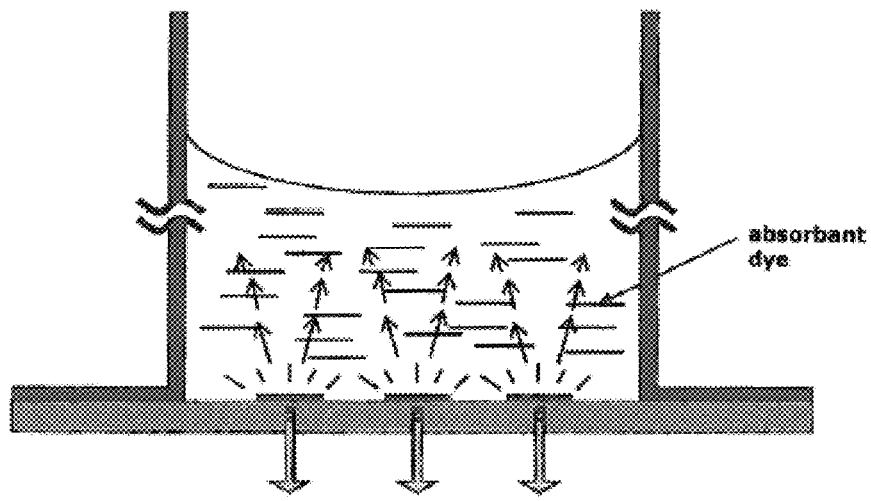

FIG. 2: Schematic cross-section of a well of a microplate. Three real dots are shown on the bottom of the well which is made of a transparent film. The hollow arrows pointing down show the really useful emission that starts towards the camera. The solid arrows represent the light path in the well and the intensity of those rays. The horizontal lines represent the dye which allows to absorb the light emitted in the liquid medium, thereby reducing the light scattering in the liquid medium and the light artifacts at the walls of the well and at the liquid/air interface and at the meniscus.

Figure 3:
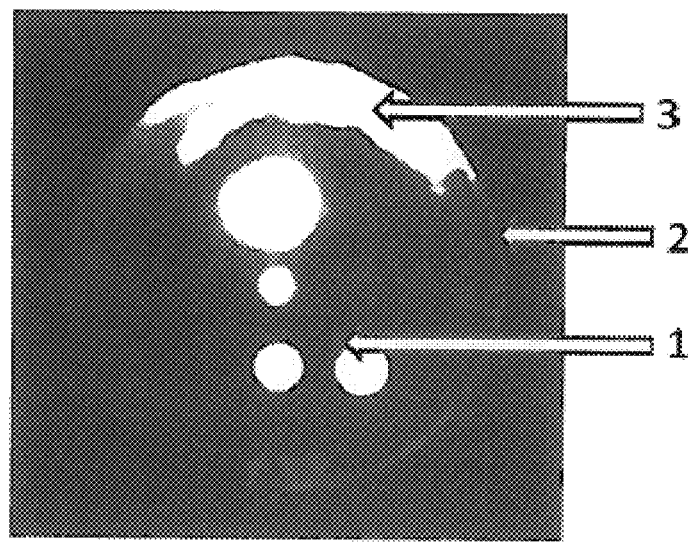

FIG. 3: Picture of a well with sample 51, without adding tartrazine. 1: luminous twin dot slightly smaller than the actual dot, the result of reflection of the real dot on the surface of liquid in the background. 2: light ring. 3: luminous arc.

Figure 4:
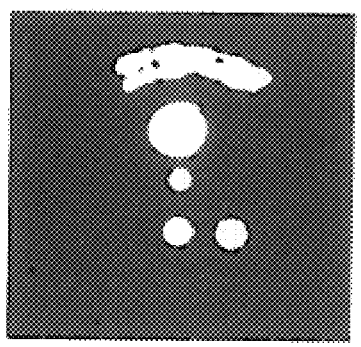

FIG. 4: Picture of a well with the sample S1, with 250 µg/ml of tartrazine.

Figure 5:
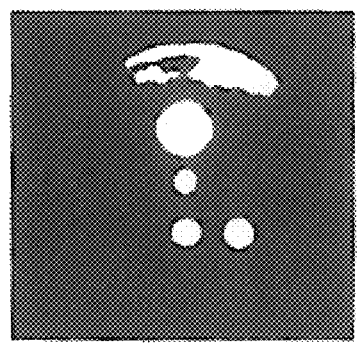

FIG. 5: Picture of a well with the sample S1, with 500 µg/ml of tartrazine.

Figure 6:
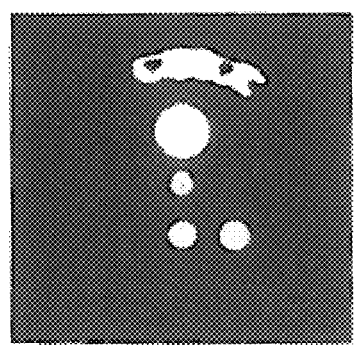

FIG. 6: Picture of a well with the sample S1, with 1000 µg/ml of tartrazine.

Figure 7:
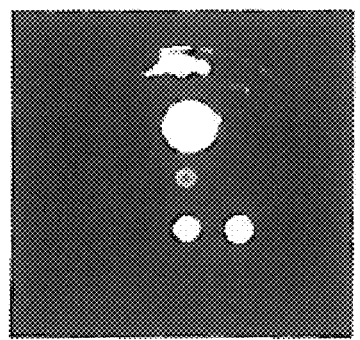

FIG. 7: Picture of a well with the sample S1, with 2000 µg/ml of tartrazine.

Figure 8:
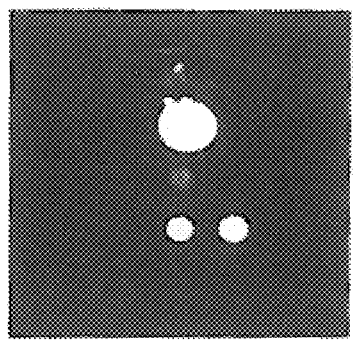

FIG. 8: Picture of a well with the sample S1, with 4000 µg/ml of tartrazine.

Figure 9:
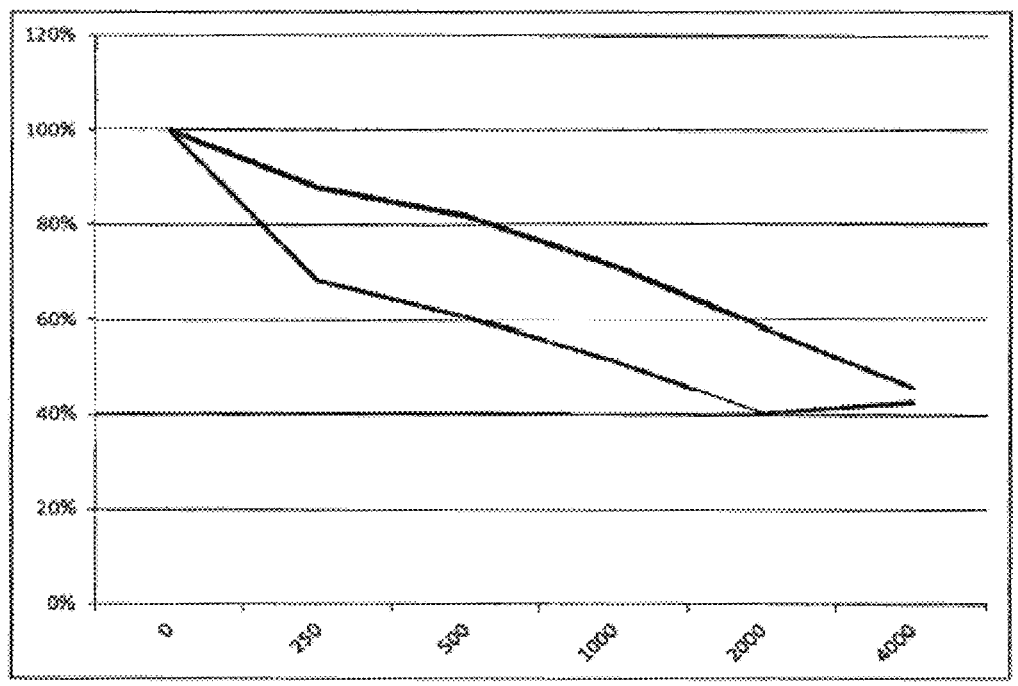

FIG. 9: Intensities normalized to the reference condition of the brightness level of the bottom of the well (lower curve) and of the signal of the reference dot (upper curve) as a function of the concentration of tartrazine (µg/ml).

Figure 10:

FIG. 10: Improvement of the ratio of detected signal to background noise depending on the concentration of tartrazine (µg/ml).

Figure 11:
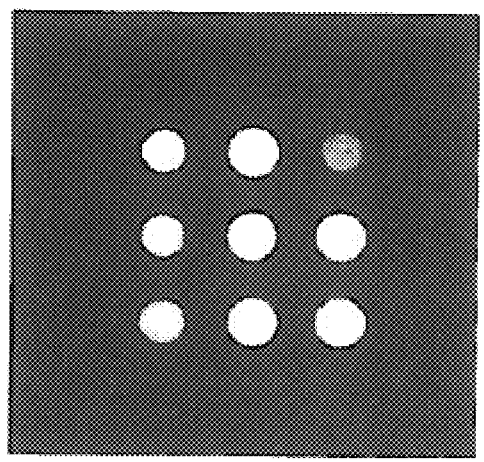

FIG. 11: Detection of fluorescence dots in the presence of the dye, said dots comprising a fluorophore as a control.

EXAMPLES

Material and Methods

A multiplex analytical method is performed using a 96-well microplate comprising 9 dots per well (3 dots numbered from 1 to 3 on the 1st line, 3 dots numbered from 4 to 6 on the 2nd line, and 3 dots numbered from 7 to 9 on the 3rd line). The dot number 9 is a reference dot (or dot Aref) comprising a carrier molecule linked to biotin. This reference dot allows, among other things, to validate the development step.

The dot number 2 comprises a specific capture ligand corresponding to the analyte AH which is present in high concentration in the reference sample S1 used.

In the analytical method, the sample S1 is contacted with the dots of a well for 40 minutes at 37° C. After washing the well, a specific detection ligand corresponding to the analyte AH present in the reference sample S1 and coupled to biotin is added to the well. After 15 minutes incubation at 37° C., the well is washed and the reporter streptavidin coupled to a peroxidase enzyme is added to the well. After 15 minutes incubation at 37° C., the well is washed. The kit "ELISTAR ETA C Ultra ELISA" (Cyanagen, Italy) is used for the development step, according to the manufacturer's manual. It consists in providing two solutions: a solution A, which comprises the substrate of the enzyme, i.e., luminol and an electron mediator (sodium 3-(10'-phenothiazinyl)propane 1-sulfonate), and a solution B, which comprises an oxidant (peroxide solution). Before acquiring the signal, a solution comprising tartrazine is added, if necessary, in the wells in the form of a mixture with solution B. After one minute of incubation with shaking at 37° C., the signal is detected.

The signal emitted by chemiluminescence by the chemiluminescent compound resulting from the enzymatic reaction is measured using an image taken by a CCD camera through a telecentric lens through the bottom of the microplate. The brightness level of the bottom of the wells is measured on the same picture.

To measure the fluorescence signal, an illumination system emitting red light centered on 620 nm wavelength illuminates the bottom surface of the solid support uniformly. A filter disposed at the entrance of the camera and having a bandwidth centered on 680 nm allows to cut off this red excitation light, letting pass the light emitted by the fluorophore present in the dots. The fluorescence signal emitted by the dots is measured using this device.

Results (i) Improvement of the Detection of the Signal in the Presence of the Dye In the case of the sample S1, a very intense light is emitted at the AH dot (dot number 2 in the grid of dots). Under the reference condition in the absence of tartrazine (see FIG. 3), there is observed, offset from the reference dot (9th dot in the grid of dots, called dot Aref), a light dot (1) of slightly lower size, result of the reflection of the reference dot on the surface of liquid in the background. There is also observed a luminous ring (2) over the entire periphery of the bottom of the well, resulting from the image of the vertical wall of the well perceived through the liquid acting as a plano-concave lens. The ring can be extremely intense near the highly bright dot AH, posing a light arc (3). A luminous veil over all the bottom of the well is also present.

Under the conditions with tartrazine, we notice the disappearance of the reflection of the dot previously observed and the disappearance of the light ring around the periphery of the well, and the reduction of the luminous veil (see FIGS. 4-8).

The signal intensity of the reference dot and the level of brightness of the well bottom were measured as the number of RLU (relative light units) (see Table 1 and FIG. 9).

TABLE 1

Intensity of the signal of the reference dot and brightness level of the well bottom

| Tartrazine concentration (µg/ml) | Intensity of the well bottom (RLU) | Intensity of the reference dot (RLU) | Background intensity (%) | Intensity of the reference dot (%) |
|---|---|---|---|---|
| 0 | 77 | 3168 | 100.0% | 100.0% |
| 250 | 53 | 2784 | 68.8% | 87.9% |
| 500 | 47 | 2592 | 61.0% | 81.8% |
| 1000 | 40 | 2262 | 51.9% | 71.4% |
| 2000 | 31 | 1854 | 40.3% | 58.5% |
| 4000 | 33 | 1455 | 43.0% | 46% |

It is observed that the luminous intensity decreases when increasing amounts of tartrazine are added. The interesting effect is that the background brightness level decreases faster than the level of the signal from the reference dot. The brightness of the bottom of the well is considered undesirable, generating a noise in the measurement of the signal which is desired to be quantified. We can thus conclude that the signal to noise ratio is improved by adding tartrazine.

TABLE 2

Signal intensity strength and brightness level

| Tartrazine concentration (µg/ml) | Intensity of the well bottom (RLU) | Intensity of the reference dot (RLU) | Ratio of intensity of reference dot to intensity of bottom of well | Improvement of the signal to noise ratio (%) |
|---|---|---|---|---|
| 0 | 77 | 3168 | 41.14 | 0.0% |
| 250 | 53 | 2784 | 52.53 | 27.7% |
| 500 | 47 | 2592 | 55.15 | 34.0% |
| 1000 | 40 | 2262 | 56.55 | 37.4% |
| 2000 | 31 | 1854 | 59.81 | 45.4% |
| 4000 | 33 | 1455 | 44.09 | 7.2% |

Table 2 and FIG. 10 show the improvement of the ratio of detected signal to background noise when increasing the concentration of tartrazine. An optimum appears to be at a concentration less or equal to 2000 µg/ml of tartrazine. Beyond this concentration, the signal is much attenuated, and the interest in adding tartrazine to improve the measurement of the signal subsides.

(ii) Detection of Dots in Fluorescence in the Presence of Dye

It was also verified that the signal emitted by a fluorophore present as a control in the dots of a microplate is well detected in the presence of a dye.

As can be seen in FIG. 11, in the presence of an absorbent solution comprising tartrazine (used at a concentration of 250 µg/ml), the detected fluorescence signal allows to define very clearly the position of the dots relative to the bottom of the well. Thus, the addition of the absorbing solution does not prevent the detection of the fluorescence signal emitted by a fluorophore present in the dots as a control.

The invention claimed is:

1. An analytical method for the detection of a signal corresponding to a presence of an analyte, comprising the following steps:
   a) providing a solid support comprising at least one compartment, said at least one compartment comprising at least one dot for detection of the analyte, wherein the at least one dot for the detection of the analyte comprises a specific capture ligand for the analyte,
   b) contacting a sample to be analyzed with the at least one dot of said at least one compartment,
   c) contacting at least one analyte detecting ligand with the at least one dot of said at least one compartment, said at least one analyte detecting ligand being coupled to a first indirect detection marker,
   d) contacting a first reporter of the first indirect detection marker coupled to said at least one analyte detecting ligand with the at least one dot of said at least one compartment, wherein the first reporter specifically binds to the first indirect detection marker, wherein the first reporter is coupled to a second indirect detection marker,
   e) contacting a second reporter of said second indirect detection marker coupled to said first reporter with the at least one dot of said at least one compartment, wherein the second reporter specifically binds to the second indirect detection marker and the second reporter is coupled to a direct detection marker,
   f) contacting one or more dyes with the at least one dot of said at least one compartment, said one or more dyes being in a liquid phase in contact with the at least one dot of said at least one compartment and wherein one of said one or more dyes is tartrazine, and wherein the one or more dyes reduce the signal corresponding to the presence of the analyte by less than 20%, and
   g) detecting the signal corresponding to the direct detection marker and correlating the signal to the presence of the analyte at the at least one dot of said at least one compartment, in the presence of the liquid phase comprising said one or more dyes.

2. The method according to claim 1, wherein the one or more dyes are tartrazine and one or more dyes selected from the group consisting of quinoline yellow, naphthol Yellow S, curcumin, riboflavin and riboflavin 5'-phosphate.

3. The method according to claim 1, wherein the signal is detected in step g) through a bottom of the solid support.

4. The method according to claim 1, wherein the signal detected in step g) is the signal emitted by a luminescent compound and/or the signal emitted by a fluorophore.

5. The method according to claim 1, wherein the one or more dyes is/are in an absorbent composition, the absorbent composition further comprising at least one compound selected from the group consisting of luminol, isoluminol, a derivative of luminol or isoluminol, a mediator of electrons, an oxidant, and a solvent.

6. The analytical method according to claim 1, wherein the method is a multiplex method comprising detecting multiple signals corresponding to the presence of multiple analytes.

7. The analytical method according to claim 1, wherein no washing step is performed between step f) and step g), and wherein step e) is performed before, after, or simultaneously with step f), so that the dye is present at the time of signal detection.

8. The analytical method according to claim 1, wherein tartrazine is present in the liquid phase at a concentration of 100 µg/ml to 3000 µg/ml.

9. The analytical method according to claim 8, wherein tartrazine is present in the liquid phase at a concentration of 200 µg/ml to 2500 µg/ml.

10. The analytical method according to claim 8, wherein tartrazine is present in the liquid phase at a concentration of 250 µg/ml to 2000 µg/ml.

11. The analytical method according to claim 8, wherein tartrazine is present in the liquid phase at a concentration of 1000 µg/ml to 2000 µg/ml.

12. The analytical method according to claim 8, wherein tartrazine is present in the liquid phase at a concentration of 2000 µg/ml.

13. The analytical method according to claim 1, wherein said liquid phase containing said one or more dyes does not emit light at wavelengths ranging from 620 to 780 nm when excited by light.

14. The analytical method according to claim 1, wherein the one or more dyes in said liquid phase do not emit light at wavelengths ranging from 620 to 780 nm when excited by light.

15. The analytical method according to claim 14, wherein the liquid phase has a basic pH.

16. The analytical method according to claim 1, wherein the one or more dyes in said liquid phase do not emit light in the red spectrum when excited by light.

17. The analytical method according to claim 16, wherein the liquid phase has a basic pH.

\* \* \* \* \*